(12) United States Patent
Piorek et al.

(10) Patent No.: US 8,515,009 B1
(45) Date of Patent: Aug. 20, 2013

(54) METAL AUTHENTICITY TESTING OF AN OBJECT USING RADIATION

(71) Applicant: Thermo Niton Analyzers LLC, Billerica, MA (US)

(72) Inventors: Stanislaw Piorek, Hillsborough, NJ (US); Stephen I. Shefsky, Brooklyn, NY (US); Michael E. Dugas, Londonderry, NH (US)

(73) Assignee: Thermo Niton Analyzers LLC, Billerica, MA (US)

( * ) Notice: Subject to any disclaimer, the term of this patent is extended or adjusted under 35 U.S.C. 154(b) by 0 days.

(21) Appl. No.: 13/627,392

(22) Filed: Sep. 26, 2012

Related U.S. Application Data

(63) Continuation of application No. 13/365,713, filed on Feb. 3, 2012.

(51) Int. Cl.
*G01N 23/223* (2006.01)

(52) U.S. Cl.
USPC .............................................. 378/45; 378/50

(58) Field of Classification Search
USPC ......................................... 378/44–46, 48–50
See application file for complete search history.

(56) References Cited

U.S. PATENT DOCUMENTS

| | | | |
|---|---|---|---|
| 4,162,528 A | | 7/1979 | Maldonado et al. |
| 6,431,748 B1 * | | 8/2002 | Baratta ............................ 374/45 |
| 7,702,067 B2 * | | 4/2010 | Grodzins et al. ................ 378/45 |
| 7,933,379 B2 | | 4/2011 | Grodzins et al. |

OTHER PUBLICATIONS

Kloos, Don, CMI International, "Analysis of Gold Karat Alloys Using Proportional Counter Based Micro-EDXRF"Prepared for International Precious Metals Institute 24th International Precious Metals Conference, Jun 2000, pp. 1-22.
Demortier, et al., "Piexe, XRF and GRT for the Global Investigation of Ancient Gold Artefacts", Nuclear Instruments & Methods in Physics Research, Section—B: Beam Interactions with Materials and Atoms, Elsevier, Amsterdam, NL, vol. 150., No. 1-4, Apr. 2, 1999, pp. 640-644.
Karydas, et al., "A compositional study of a museum jewellery collection (7th—1st BC) by means of a portable XRF spectrometer" Nuclear Instruments & Methods in Physics Research, Section—B: Beam Interactions with Materials and Atoms, Elsevier, Amsterdam, NL, vol. 226, No. 1-2, Nov. 1, 2004, pp. 15-28.
Trojek, et al., "X-Ray fluorescence analysis of archaeological finds and art objects: Recognizing gold and gliding", Applied Radiation and Isotopes, vol. 70, No. 7, Mar. 29, 2012, pp. 1420-1423.
European Search Report, Application No. EP 13 15 0710, dated May 17, 2013, pp. 1-7.

* cited by examiner

*Primary Examiner* — Jurie Yun
(74) *Attorney, Agent, or Firm* — Chapin IP Law, LLC

(57) ABSTRACT

Techniques disclosed herein include systems and methods for identifying counterfeit gold jewelry and other counterfeit gold items. Techniques include determining—using a non-destructive mechanism—whether an item of interest (such as an article represented as true gold) is solid gold or a gold-plated object. Techniques include using an X-ray fluorescence (XRF) analyzer to differentiate true gold from gold plating. The XRF analyzer can distinguish between gold plating and bulk gold material by comparing a ratio of L-alpha and L-beta x-ray lines of gold. The analyzer measures a ratio of intensities of characteristic L-lines of gold using X-ray fluorescence (XRF) spectroscopy. When implemented using an XRF analyzer, the system nondestructively determines whether a test object is made of solid gold/gold alloy or has gold plating only.

31 Claims, 4 Drawing Sheets

METAL AUTHENTICITY TESTING OF AN OBJECT USING RADIATION

RELATED APPLICATIONS

This Patent Application is a Continuation of and claims priority to U.S. patent application Ser. No. 13/365,713 filed on Feb. 3, 2012, entitled, "SYSTEM AND METHOD FOR IDENTIFICATION OF COUNTERFEIT GOLD JEWELRY USING XRF", the entire teachings of which are incorporated herein by this reference.

BACKGROUND

The present invention relates to methods for determining the concentration of a specified elemental substance employing x-ray fluorescence techniques, and, more particularly, to methods for determining elemental concentrations of precious metals.

Ornamental gold jewelry is typically made from just a handful of gold alloys. Such gold alloys include gold as a major component, which is most often combined with other metals such as copper, zinc, silver and nickel. Gold jewelry that is composed of either solid gold or a solid gold alloy, is relatively expensive compared to other types of jewelry. Less expensive jewelry is often produced of a common alloy such as brass (or sometimes silver). This common alloy is then plated or clad with layer of gold or a layer of gold alloy. To comply with laws governing gold commerce, such jewelry must be properly marked to indicate the type and quality of the gold layer. For example, such labels can include "gold plated" or "gold electroplated" for plated objects, as well as "gold filled" for objects made of gold-clad brass or silver. In a specific example, gold-plated sterling silver is a recognized jewelry material as long as a given gold-plated sterling silver item is recognized as such.

Gold prices, especially recently, have been rising at an accelerated rate. The rise in gold prices is accompanied by a high demand for gold. Due to the high demand for gold and its accompanying high price, the jewelry market is flooded with brass and copper articles plated with thin layers of gold purporting to be gold objects, but instead are fakes. While such gold-plated articles are legitimate and permissible under trade laws when accurately identified as a plated object, significant amounts of gold-plated articles are being passed off as, or are being identified as, being made of solid gold, or a solid gold alloy. Gold-plated items can be offered for sale, for example, to a gold reseller, such as in the case of a consumer selling personal jewelry items for cash. During a purchase of a gold item (such as gold jewelry), the purchaser typically evaluates the gold to determine its worth. This is usually a very fast process that does not permit detailed analysis. It is common for gold purchasers to purchase items represented as solid gold or as a solid gold alloy, when in reality the purchased items are instead simply gold-plated metal. Purchasing gold-plated items when represented as solid gold or solid gold alloy results in a significant loss from a purchase transaction. Accordingly, there is a need for a quick and accurate method of detecting counterfeit gold.

SUMMARY

Conventional techniques for verifying bulk gold are partially destructive and/or time consuming in nature. Such conventional techniques can include acid tests and scratch tests. For example, with a scratch test a file is used to scratch the surface of a gold item. After the gold item is scratched, the gold item can then be visually inspected to determine if there is a substrate made of a different material or different alloy. Such scratch tests are a destructive technique. In cases where a scratched gold item turns out to be solid gold, then the value of the gold item would be reduced and/or need subsequent restoration. An acid test is similarly destructive because a sample from a gold item needs to be taken to determine a karat value and/or substrate composition. In many gold-buying situations, such testing is either unavailable, too time-consuming to keep up with a purchase transaction rate, or undesirable due to its destructive nature. After purchases are completed, purchased gold items can be tested (possibly at a location other than the purchase site) to verify that the purchases are indeed gold or gold alloy. Unfortunately, without testing prior to purchase, it is possible to purchase gold items as true gold when the gold items are in reality gold-plated. This means that purchasers might pay 10, 100 or 1000 times more then the gold items are actually worth.

Techniques disclosed herein include systems and methods for identifying counterfeit gold jewelry. Techniques include determining—using a non-destructive mechanism—whether an item of interest (such as an article represented as true gold) is solid gold or gold-plated, among other things. Techniques include using x-ray analyzers to differentiate true gold from gold plating. An analyzer uses x-ray fluorescence by reading a spectrum of x-rays returning from a bulk material. The analyzer can detect metals in the substrate material (below any gold-plating). These detected metals can include lead, copper, zinc, silver, or other substrate materials. The analyzer can distinguish between gold plating and bulk gold material by comparing a ratio of L-alpha and L-beta x-ray lines of gold from gold plating to that of the bulk gold material.

One embodiment includes an X-ray fluorescence (XRF) analyzer that executes a counterfeit gold detection process or system. An XRF analyzer directs an x-ray excitation beam onto at least a portion of an item of interest, such as a gold item represented as solid gold. The x-ray excitation beam is directed such that the x-ray excitation beam causes the item of interest to fluorescently emit x-rays at various energies characteristic for the metallic elements contained in the item of interest. The XRF analyzer then measures an intensity of a first energy (L-alpha) that corresponds to gold (has characteristic atomic signature of gold). This first energy is identified from x-rays fluorescently emitted from the item of interest. The XRF analyzer also measures an intensity of a second energy (L-beta) that corresponds to gold. This second energy is identified from x-rays fluorescently emitted from the item of interest. The XRF analyzer can then calculate a ratio of measured intensities between the intensity of the first energy and the intensity of the second energy. In response to identifying that the calculated ratio is beyond a predetermined value, the XRF analyzer indicates that the item of interest is gold-plated. Such an indication can mean counterfeit gold when the item of interest is represented as solid gold instead of as gold-plated. The XRF analyzer can be embodied as a process, as a device (such as a portable testing device), or otherwise.

Other embodiments herein include software programs to perform the steps and operations summarized above and disclosed in detail below. One such embodiment comprises a computer program product that has a computer-storage medium (e.g., a non-transitory, tangible, computer-readable media, disparately located or commonly located storage media, computer storage media or medium, etc.) including computer program logic encoded thereon that, when performed in a computerized device having a processor and corresponding memory, programs the processor to perform (or causes the processor to perform) the operations disclosed herein. Such arrangements are typically provided as software, firmware, microcode, code data (e.g., data structures), etc., arranged or encoded on a computer readable storage medium such as an optical medium (e.g., CD-ROM), floppy disk, hard disk, one or more ROM or RAM or PROM chips, an Application Specific Integrated Circuit (ASIC), a field-programmable gate array (FPGA), and so on. The software or firmware or other such configurations can be installed onto a computerized device to cause the computerized device to perform the techniques explained herein.

Accordingly, one particular embodiment of the present disclosure is directed to a computer program product that includes one or more non-transitory computer storage media having instructions stored thereon for supporting operations such as: directing an x-ray excitation beam onto at least a portion of an item of interest such that the x-ray excitation beam causes the item of interest to fluorescently emit x-rays at various energies; measuring an intensity of a first energy that corresponds to gold, the first energy identified from x-rays fluorescently emitted from the item of interest; measuring an intensity of a second energy that corresponds to gold, the second energy identified from x-rays fluorescently emitted from the item of interest; calculating a ratio of measured intensities between the intensity of the first energy and the intensity of the second energy; and in response to identifying that the calculated ratio is beyond a predetermined value, indicating that the item of interest is gold-plated. The instructions, and method as described herein, when carried out by a processor of a respective computer device, cause the processor to perform the methods disclosed herein.

Other embodiments of the present disclosure include software programs to perform any of the method embodiment steps and operations summarized above and disclosed in detail below.

Of course, the order of discussion of the different steps as described herein has been presented for clarity sake. In general, these steps can be performed in any suitable order.

Also, it is to be understood that each of the systems, methods, apparatuses, etc. herein can be embodied strictly as a software program, as a hybrid of software and hardware, or as hardware alone such as within a processor, or within an operating system or within a software application, or via a non-software application such as person performing all or part of the operations.

As discussed above, techniques herein are well suited for use in software applications supporting identification of gold plating. It should be noted, however, that embodiments herein are not limited to use in such applications and that the techniques discussed herein are well suited for other applications as well.

Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Note that this summary section herein does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives of the invention and embodiments, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein as illustrated in the accompanying drawings in which like reference characters refer to the same parts throughout the different views. The drawings are not necessarily to scale, with emphasis instead being placed upon illustrating the embodiments, principles and concepts.

DETAILED DESCRIPTION

Figure 1:
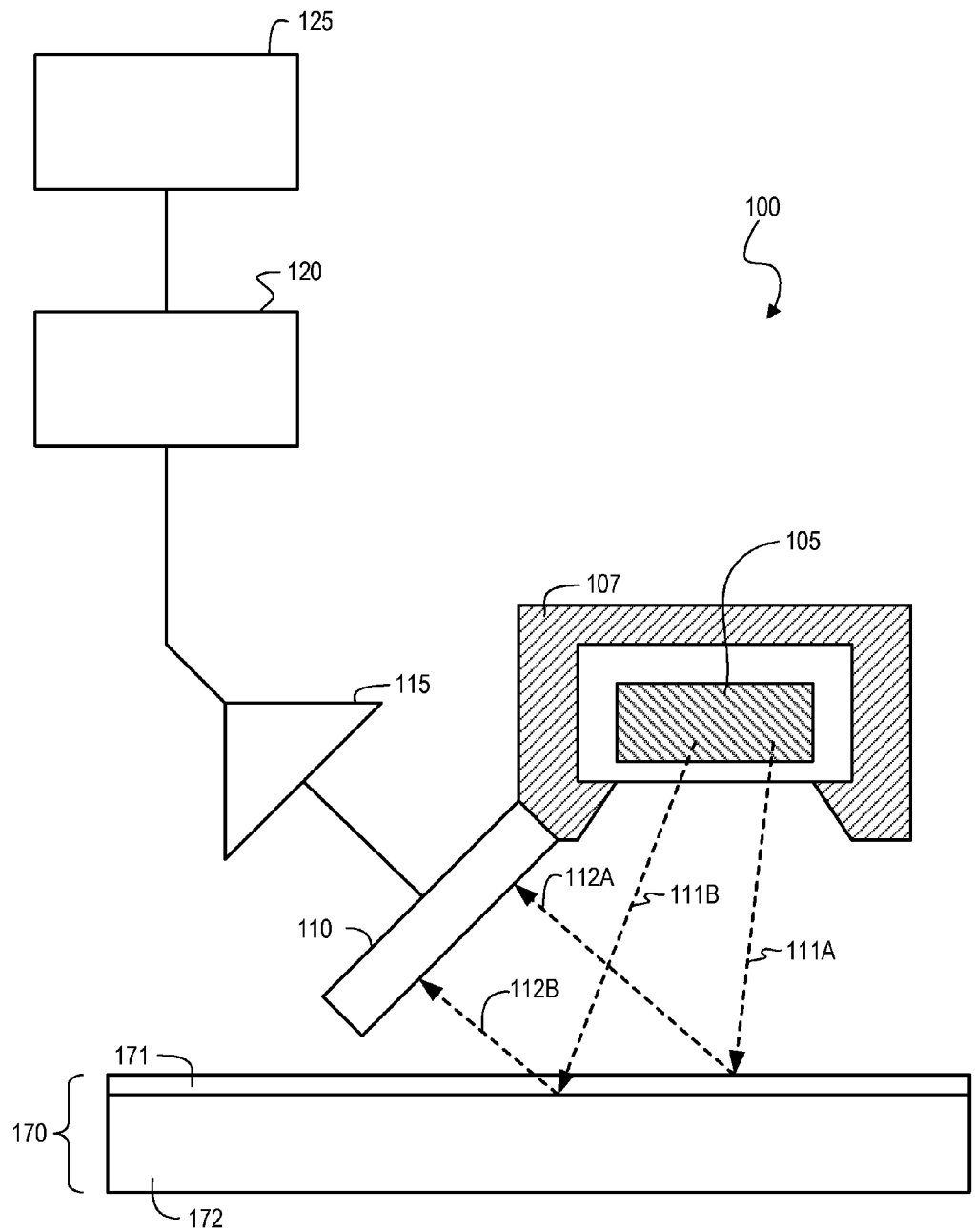
FIG. 1 is a schematic view of an instrument for detecting gold plating according to embodiments herein.

Techniques disclosed herein include systems and methods for identifying counterfeit gold jewelry and other counterfeit gold items. Techniques include determining—using a non-destructive mechanism—whether an item of interest (such as an article represented as true gold) is solid gold or gold-plated, among other things. Techniques include using an x-ray analyzer to differentiate true gold from gold plating. The analyzer uses x-ray fluorescence by reading a spectrum of x-rays returning from a bulk material. The analyzer can detect metals in the substrate material (below any gold-plating). These detected metals can include lead, copper, zinc, silver or other substrate materials. The analyzer can distinguish between gold plating and bulk gold material by comparing a ratio of L-alpha and L-beta x-ray lines of gold. The analyzer measures a ratio of intensities of characteristic L-lines of gold using X-ray fluorescence (XRF) spectroscopy. When implemented using an XRF analyzer, the system non-destructively measures the ratio of the L-lines of gold excited in a test object and determines whether the test object is made of solid gold/gold alloy or has gold plating only.

X-ray fluorescence involves directing x-rays from an external source such as x-ray tube at a material or item of interest. These external x-rays interact with atoms of the material or item of interest. Some of the x-rays can knock out the electrons from a lower energy shell of the atom, which results in electrons from a higher shell filling the gap. This process causes a release of energy, by the atom, in the form of an x-ray photon, whose energy is characteristic and unique to the atom of the given element. Photons released from atoms of the material can then be detected and identified. Each element has its own, unique x-ray signature. A given x-ray tube can produce a continuum of x-ray energies. The XRF analyzer can then filter out energies that are not needed for a particular elemental analysis.

Conventional XRF analyzers cannot detect gold plating. XRF analyzers can determine composition of gold alloys used for manufacture of jewelry and its karatage—especially when the number of gold alloys in use is rather small (10 to 15). XRF analysis of a gold alloy assumes that the analyzed object is made of homogeneous material. If the object presented for analysis by XRF is made of brass and plated with gold, then a conventional XRF analyzer has no means to determine the existence of gold plating. Consequently, conventional XRF analytical software treats the object as homogeneous. Such treatment results in erroneous analysis.

According to techniques and discoveries disclosed herein, characteristic L-series X-rays of gold have a penetration depth in pure and karat gold of approximately 10 to 12 micrometers (microns, μm). The two major gold lines, L-alpha and L-beta, have different energies, 9.71 and 11.45 keV, respectively. Accordingly, the L-alpha line is absorbed much stronger by a given medium of gold as compared to the L-beta line. In a relatively thin layer of pure gold that can vary its thickness (for example, from, say 0.5 μm to 20 μm in 1 μm steps), intensities of both L-lines can be measured. By observation, both intensities monotonically increase with thickness of gold layer until each of them reaches its respective "saturation" plateau at about 15 to 20 μm (a self absorption effect). Beyond this thickness of gold, there is essentially no additional increase of intensities. Thus, absorption of both L-lines suffers with an increased thickness of gold. Note, however, that because the L-alpha line is less energetic, the L-alpha line reaches its saturation plateau at faster rate than the more energetic L-beta line. Consequently, a ratio of the two lines at any given thickness between 0 to about 15 μm is not a constant, but instead varies with the thickness.

Figure 2:
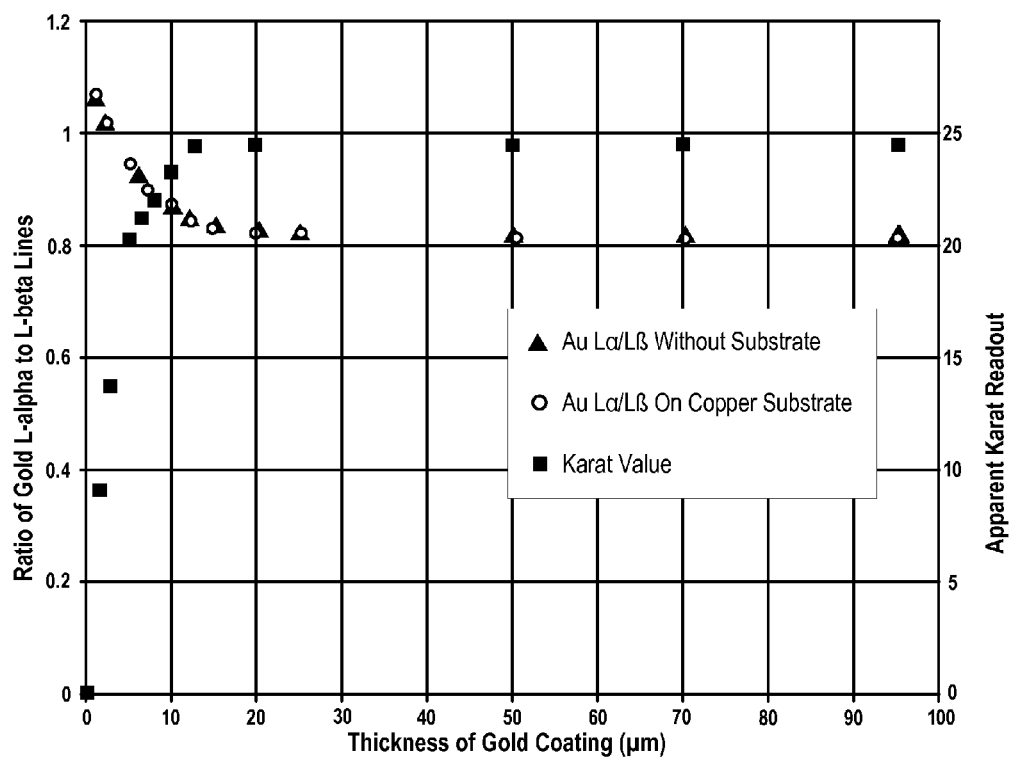
FIG. 2 is a plot diagram showing a ratio of gold x-ray lines as a function of plating thickness.

FIG. 2 illustrates this variation of ratio values as a function of gold thickness. FIG. 2 shows empirical data obtained with a hand-held XRF analyzer. Ratio values resulting from XRF analysis of gold (Au) with no substrate are shown on the graph as solid triangles. Ratio values resulting from XRF analysis of gold on a copper substrate are shown on the graph as circles. Beginning at a thickness of zero, the ratio decreases exponentially until reaching about 12-15 microns. Once a thickness of the gold layer exceeds a thickness of approximately 15 microns, the ratio of the two lines does not change significantly. This ratio represents the value for homogeneous or "infinitely" thick pure gold. Also note that the change in ratio value is independent of having a substrate or type of substrate. For example, similar results were discovered when testing on a brass substrate and testing of gold foil without a substrate. FIG. 2 also shows the relationship of an apparent karat readout (shown with black squares) as compared to the calculated ratio values. While karat values can be obtained using bulk material XRF analysis, gold line ratio values can also be used to determine an approximate karat value of an item of interest. This apparent karat value and/or the ratio value can be used to identify a thickness of gold plating on an object identified as having gold plating.

The relationship between the ratio of the two lines as a function of gold thickness can be used by an XRF analyzer as an indicator of gold plating. In other words, this ratio and an XRF analyzer can be used to identify counterfeit gold items. Such identification is effective up to about a 10-12 micron thickness of gold plating.

The XRF analyzer disclosed herein can also be used with karat gold and karat gold plating. Gold karatage is an indication of a percentage composition or concentration of gold in a given gold alloy. Gold karat values use a linear system to represent percent composition. For example, 24K gold means 100% gold, 12K gold means 50%, and 14 karat gold means 58.3% gold. The XRF analyzer can determine a composition of all materials in a target object, and, based on the gold composition percentage, return a karat value. In the jewelry trade, there are various legal gold percentages that can be identified and sold as jewelry. For example, some countries require at least 9 or 10 karats of gold to qualify as a gold alloy for a solid material or plating. This means that if gold is detected as, for example, 7 karat gold, then this indicates that a corresponding item is not a valid gold alloy. Such a low karat value can mean either a low gold percentage, or very thin gold plating applied to a given, non-gold object.

10, 12 and 14 karat gold has been commonly used in jewelry to manufacture gold-plated articles. In practice, gold-plating of jewelry and consumer items is rarely thicker than 8 microns. As such, the XRF analyzer disclosed herein is well suited for analyzing the vast majority of gold items and detecting gold plating with high accuracy. There are various classifications of gold plating. Gold flash is about 0.175 microns. Gold electroplate is about 0.5 microns, and used for costume jewelry, pendants, eyeglasses, etc. Gold plate is 1.0 microns and heavy gold plate is 2.8 microns. Gold plate and heavy gold plate are used for bracelets, trophies, cutlery, cuff links, vermeil jewelry, medals, etc. Specialty gold plate of 3-8 microns can be used with liturgical items, exterior architecture, ceremonial military items, medallions, etc. Electroforming is 10 or more microns and used with scientific equipment, luxury watches, and some exterior architectural applications. Thus, most jewelry items having gold plating are typically 1-8 microns thick, and, therefore, can be accurately identified by the XRF analyzer disclosed herein as plated.

Referring now to FIG. 1, a schematic illustration shows an XRF analyzer 100 for identifying gold plating. An x-ray source 105 generates an x-ray excitation beam including photons 111A and 111B. Photons 111A and 111B are directed onto or toward a least a portion of an item of interest 170. Item of interest 170 includes a substrate layer 172 and a gold plating layer 171. Note that this combination of substrate and gold plating is exemplary. Other items of interest could be a homogeneous gold alloy without plating. Photons 111A and 111B can be of two different energies. Photons 111A and 111B collide with item of interest 170. These photons have energy sufficient to eject one or more electrons from atoms of the item of interest 170. As a consequence, atoms having electrons ejected fluoresce by re-emission of radiation at a different energy as shown with photons 112A and 112B. An x-ray detector 110 is positioned to receive x-rays emitted from the item of interest. The emitted x-rays included fluorescently emitted x-rays at a first energy (112A) that corresponds to gold, the emitted x-rays also included fluorescently emitted x-rays at a second energy (112B) that corresponds to gold, that is, that corresponds to signature characteristics of the gold atom.

A signal processor 120 is coupled to detector 110. Signals from the detector 110 can be amplified by amplifier 115 prior to being received at the signal processor 120. A shield 107 can protect the detector 110 from direct radiations of source 105. The detector 110 can detect a spectrum of photons including fluorescent x-rays and photons from the source 105 that are scattered by the item of interest 170. The signal processor 120 calculates a ratio of measured intensities between an intensity of the first energy and an intensity of the second energy (gold L-alpha line and gold L-beta line). User interface or display 125 can then display an indication that the item of interest is gold-plated in response to the signal processor 120 identifying that the calculated ratio is beyond a predetermined value.

Additional background description and use of XRF analyzers in general can be found in U.S. Pat. No. 7,933,379, issued to Grodzins and entitled, "Measurement of lead by X-ray fluorescence," which is hereby incorporated by reference.

Figure 3:
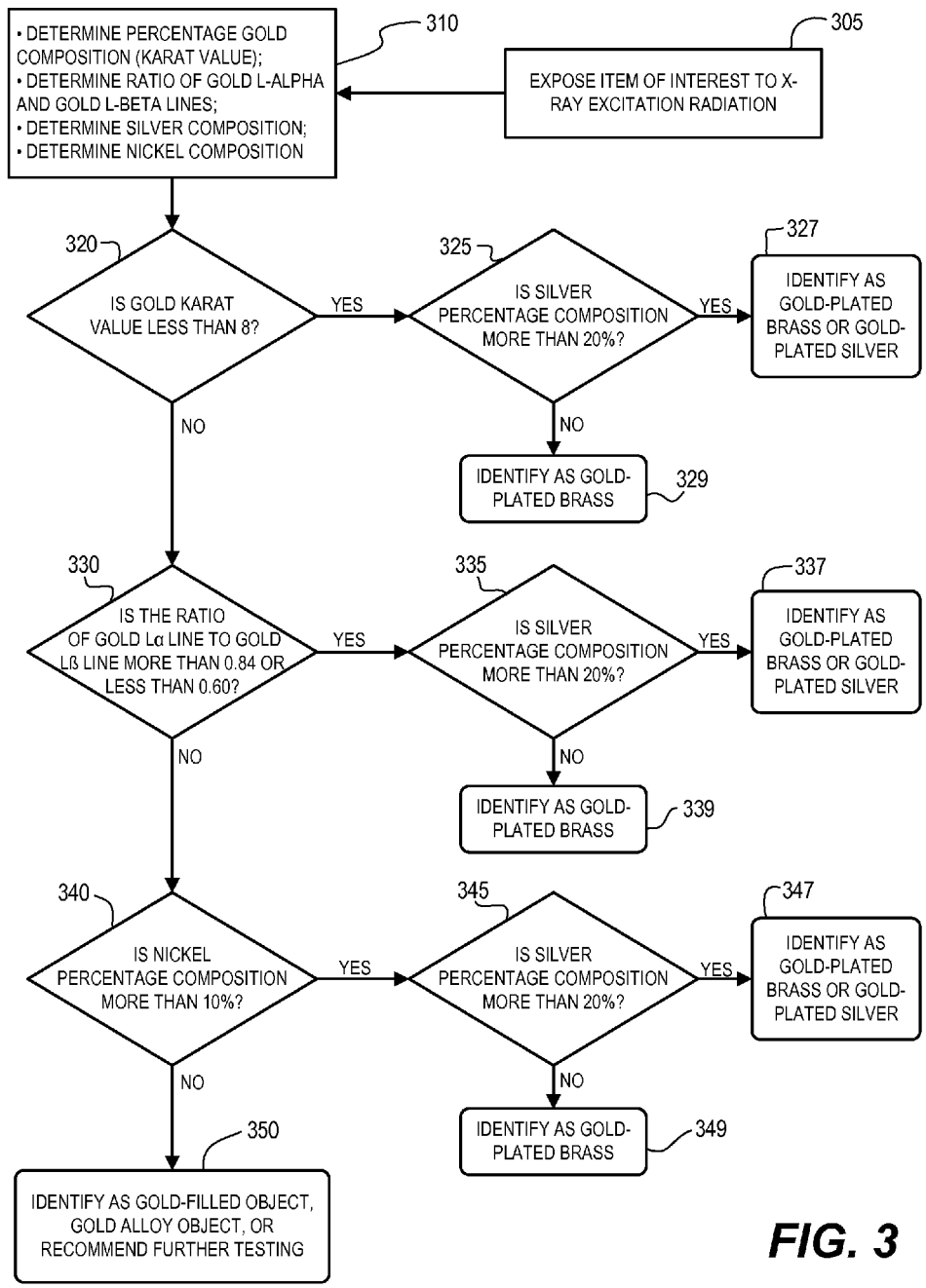
FIG. 3 is a flowchart illustrating an example of a process supporting gold plating detection according to embodiments herein.

FIG. 3 is a flow chart of logical process steps that the XRF analyzer can execute as part of its method for identifying gold plating. In step 310, the XRF analyzer analyzes emitted radiation from the item of interest 170 and identifies multiple items of information corresponding to the item of interest. This identification includes steps that: (1) determine a percentage gold composition (karat value), (2) determine a ratio of gold L-alpha and gold L-beta lines, (3) determine a silver composition (percentage/concentration), and (4) determine a nickel composition (percentage/concentration). With these items of information identified or calculated, the XRF analyzer can evaluate this information to identify any gold plating. A corresponding device can be calibrated for bulk alloy analysis to calculate all percentages of metals.

In step 320 the XRF analyzer identifies if the gold karat value is less than about 8 (less than 33% gold). With a gold karat value less than about 8, the XRF analyzer then identifies in step 325 whether the silver composition is more than 20%. If the silver composition is more than about 20% then the XRF analyzer identifies the item of interest as either gold-plated brass or gold-plated silver (327). If the silver composition is less than about 20% then the XRF analyzer identifies the item of interest as gold-plated brass (329). In other embodiments, the XRF analyzer can identify different substrate materials, or simply identify that the substrate is not a gold alloy or legal gold alloy. The vast majority of gold plated jewelry items have plating on either brass or silver, though it can be possible for gold to be plated on other substrates. Note that the item of interest is a metallic item that has either been represented as a gold item (such as by an individual), or has the appearance of gold (at least on the surface).

Gold plating can be very thin, and when combined with a substrate may return a reading of 10% gold (2.4 karat). In this case it is easily determined that an item of interest is not a gold alloy because the gold percentage is too low. That is, even if the item of interest were a solid alloy having a low percentage of gold throughout, such a low karatage is not considered as a legal gold alloy, and is thus a counterfeit gold alloy or a gold plated object. In either case it can be deemed counterfeit. Note that if the object of interest happened to be a solid alloy having, for example, 10% gold, then this item of interest could nevertheless have some value as an object from which gold can be extracted, but could not be legally represented as a gold alloy or jewelry item. This can be used as a first indication that an item of interest being analyzed is a plated object. With such a result it is optional whether to look at the ratio of lines because this low karatage determination can be sufficient to conclude gold plating. In another case, the gold content may be identified as 8 or 9 karat. At this point there needs to be more than a karatage analysis to identify gold plating because such karatage is close to what is allowed on the market. In this case the system then looks to the ratio of the two lines to decide whether an item is plated.

In step 330 the XRF analyzer identifies whether the ratio of gold L-alpha line to gold L-beta line is more than 0.84 or less than 0.60. That is, whether the ratio value is outside of the range of 0.61-0.84. The ratio value can be calculated from net intensities. With a ratio value more than 0.84 or less than 0.60, the XRF analyzer continues to step 335. In step 335 the XRF analyzer then identifies whether the silver composition is more than 20%. If the silver composition is more than about 20% then the XRF analyzer identifies the item of interest as either gold-plated brass or gold-plated silver (337). If the silver composition is less than about 20% then the XRF analyzer identifies the item of interest as gold-plated brass (339). Note that some gold plated objects can mimic a 14 karat gold piece, and so relying on a karat analysis alone may be insufficient to accurately verify plating. Using the ratio analysis, however, XRF analyzer can identify seemingly 14 karat gold objects that are in reality gold-plated objects. When gold plating thickness approaches zero thickness, FIG. 2 teaches that the ratio of gold lines should reach a value of approximately 1.1. However, when the plating is extremely thin, such as less than approximately 0.2 microns, the net intensities of gold lines are very small and as such they are measured with large uncertainty. Consequently, the measured intensity of the first gold line may be much smaller than the measured intensity of the second gold line resulting in the ratio much smaller than the predetermined value of 0.84. That is why the ratio value of 0.60 can be used as an additional technique to verify gold plating. Such low ratios are the result of extremely thin gold plating. The exact numerical values of the predetermined ratios are specific to a given XRF analyzer for which they were determined. By way of a non-limiting example, other XRF analyzers may analyze gold lines such that a gold line ratio threshold (beyond which gold plating is concluded) could be 0.63, 0.77, 0.86, etc. Other XRF analyzers can use different values although it is not expected that the various XRF analyzers will differ much from the examples described herein. In any XRF analyzer, the basic technique is the same in that after experimentation and/or calibration, an XRF analyzer can be configured for detected gold plating according to its respective x-ray detection and measurement mechanisms. Changing ratio values can be identified until a thickness reaches about 15 microns of gold/gold alloy, after which the ratio becomes substantially constant.

In step 340, the XRF analyzer identifies whether the nickel percentage composition is more than 10%. With a nickel composition more than 10%, the XRF analyzer continues to step 345. In step 345 the XRF analyzer then identifies whether the silver composition is more than 20%. If the silver composition is more than about 20% then the XRF analyzer identifies the item of interest as either gold-plated brass or gold-plated silver (347). If the silver composition is less than about 20% then the XRF analyzer identifies the item of interest as gold-plated brass (349). With a nickel composition less than 10%, the XRF analyzer identifies the item as either gold-filled, gold alloy, or otherwise recommend further testing.

Calculating a percentage of silver or nickel can be important because these metals are commonly used in gold alloys. The ratio of these metals, therefore, can provide additional certainty of an object that is plated. Legitimate plating of gold on brass often includes a layer of nickel over the brass to prevent the copper in the brass from diffusing into the gold plating, which diffusion can change a plating color or corrode the plating. Silver also has a similar tendency to diffuse into gold plating. A Gold-filled object refers to an object with very thick gold plating, such as substantially more than 20 microns. In such situations more testing may be necessary because, although the item may not be gold plated, the item could still be gold filled instead of a bulk gold alloy.

Thus, an XRF analyzer can be used to differentiate true gold from gold plating. Such techniques are accurate up to about 10-15 microns of gold plating thickness. Gold plating above 10-15 microns can be sufficiently thick to attenuate x-rays coming from a substrate on which the gold plating is applied. While gold plating in certain items can exceed 15 microns, jewelry gold and decorative gold items tend to be relatively thin, that is, typically less than about 5-8 microns. With such relatively thinner gold plating, it is possible for some x-rays to penetrate the gold plating to reflect off of the substrate and provide for relatively quick and nondestructive verification of gold-plating.

Figure 4:
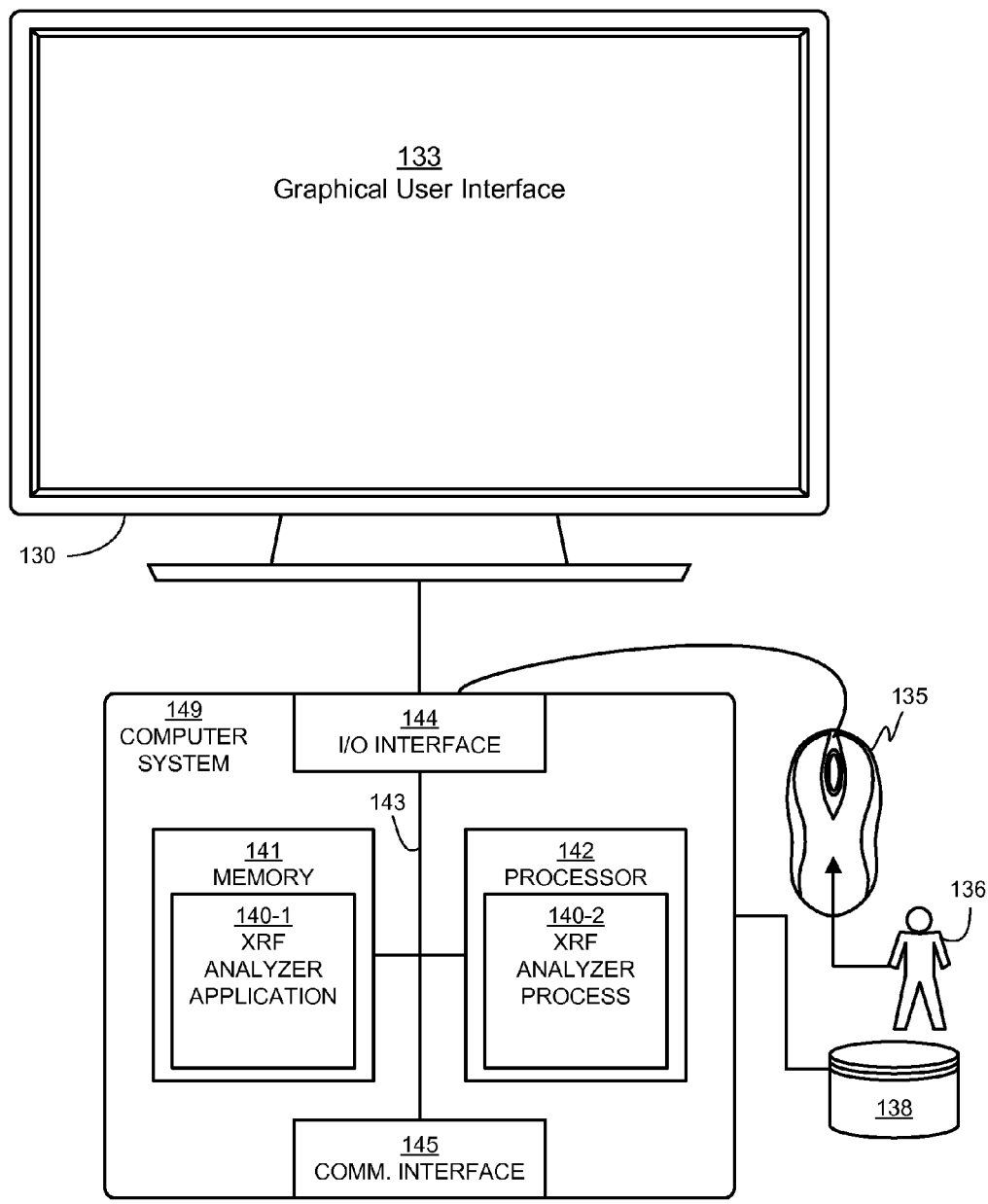
FIG. 4 is an example block diagram of a XRF analyzer operating in a computer/network environment according to embodiments

FIG. 4 illustrates an example block diagram of an XRF analyzer 140 operating in a computer/network environment according to embodiments herein. In summary, FIG. 4 shows computer system 149 displaying a graphical user interface 133 that provides an XRF analyzer interface. Computer system hardware aspects of FIG. 4 will be described in more detail following a description of the flow charts.

Functionality associated with XRF analyzer 140 will now be discussed via various embodiments. One embodiment includes a method for identifying gold plating on objects by x-ray fluorescence (XRF). The XRF analyzer directs an x-ray excitation beam onto at least a portion of an item of interest such that the x-ray excitation beam causes the item of interest to fluorescently emit x-rays at various energies. For example, a user manipulating a hand-held device can target a gold necklace, bracelet, ring, etc., so that the item of interest is in the path of emitted x-rays. The XRF analyzer measures an intensity of a first energy that corresponds to gold. This first energy is identified from x-rays fluorescently emitted from the item of interest. The XRF analyzer also measures an intensity of a second energy that corresponds to gold. This second energy is identified from x-rays fluorescently emitted from the item of interest. Energies corresponding to gold refer, for example, to photon energies having an energy signature characteristic of elemental gold. The XRF analyzer calculates a ratio of measured intensities between the intensity of the first energy and the intensity of the second energy. By way of a non-limiting example, such a ratio can include gold L-alpha lines to gold L-beta lines, that is, characteristic fluorescent emission lines or signature lines.

In response to identifying that the calculated ratio is beyond a predetermined value, the XRF analyzer or signal processor can indicate via a display that the item of interest is gold-plated. For example, a handheld scanner can emit an audible alert, flash a light, or otherwise display text indicating that the item of interest appears to be gold plated. If a given seller of the item of interest represented the item of interest as a homogenous gold alloy, but the XRF analyzer identifies the item of interest as a gold-plated item, then an operator can conclude that the item of interest is a counterfeit or fake gold item. Note that the predetermined ratio value beyond which the XRF analyzer can identify gold plating can be a ratio value relative to how the ratio was computed. For example, example embodiments herein calculate a ratio of gold L-alpha to gold L-beta lines. An equivalent technique, however, would be to calculate a ratio of gold L-beta lines to gold L-alpha lines, and then change the threshold value accordingly, or calculate an inverse ratio, etc.

In other embodiments, the XRF analyzer uses a value of 0.84 as the predetermined ratio value. The XRF analyzer can alternatively identify that the calculated ratio is less than a second predetermined value and, in response, indicate that the item of interest is gold-plated. This second predetermined value can be a ratio value of approximately 0.60. In other words, if the XRF analyzer identifies that the ratio value is either more than 0.84 or less than 0.6, then the XRF analyzer can identify the item as gold-plated.

In other embodiments, the predetermined value is a gold lines intensity ratio representing a gold thickness of more than about 15 microns. This gold lines intensity ratio essentially represents gold of infinite thickness. Thus, the calculated ratio of measured intensities (gold lines ratio measured from the item of interest) can be compared to the gold lines intensity ratio representing gold that is thicker than about 15-20 microns. If the calculated ratio is about the same as the gold lines ratio for thick gold, then the system can determine no gold plating. If, however, there is a difference in the ratio the then XRF analyzer can determine gold plating. An actual value of the gold lines intensity ratio can be initially set in an XRF analyzer device, or set after being calibrated by testing on sufficiently thick gold. With some XRF analyzer devices this value may be about 0.84, while other devices may different. Regardless of the particular device, this predetermined value represents or corresponds to a gold thickness of more that about 15 microns, which is used for comparison to gold lines ratios observed from various gold test objects. With a gold thickness more than about 15 microns, the atomic properties of gold are such that when gold atoms located deeper than about 15 microns fluoresce, the released photons from these gold atoms are absorbed by surrounding gold atoms, thereby preventing such photons from escaping a gold surface. Accordingly, the calculated ratio being beyond (greater than or less then depending on a particular calculation technique) the predetermined value indicates a thickness of gold less that about 15 microns, meaning that there is gold plating.

The XRF analyzer can identify a percentage composition of gold from the item of interest relative to other elements in the item of interest by analyzing a spectrum of x-rays fluorescently emitted from the item of interest. In response to identifying that the concentration of gold is less than about 33 percent, the XRF analyzer can indicate (or confirm) that the item of interest is gold-plated. In some embodiments, this can be a first test to indicate gold plating. If a gold percentage is sufficiently low, then a ratio analysis may not be necessary because the karatage is sufficiently low such that the item of interest is either gold plated or a fake/illegal gold alloy Likewise, the XRF analyzer can identify a percentage composition of nickel from the item of interest relative to other elements in the item of interest by analyzing the spectrum of x-rays fluorescently emitted from the item of interest. In response to identifying that the concentration of nickel is greater than about 10 percent, the XRF analyzer can indicate that the item of interest is gold-plated. Identifying a percentage composition of gold and or other elements can be executed using bulk analysis of elemental composition of the item of interest using an energy dispersive XRF analyzer or a wavelength dispersive XRF analyzer.

The XRF analyzer can identify a percentage composition of silver from the item of interest relative to other elements in the item of interest by analyzing the spectrum of x-rays fluorescently emitted from the item of interest. In response to identifying that the concentration of silver is less than about 20 percent, the XRF analyzer can indicate that the item of interest is gold-plated brass. In response to identifying that the concentration of silver is greater than about 20 percent, the XRF analyzer can indicate that the item of interest is either gold-plated brass or gold-plated silver. In addition to indicating that the item of interest is gold-plated, the XRF analyzer can indicate an approximate thickness of gold plating on the item of interest based on the calculated ratio of gold lines.

In another embodiment, the XRF analyzer can function primarily as a software process for identifying gold plating on objects from x-ray fluorescence (XRF). In such a process the XRF analyzer can execute on an XRF device, or process XRF data remotely. Such an embodiment includes receiving data corresponding to x-rays that have been fluorescently emitted at various energies from an item of interest, receiving an intensity of a first energy that corresponds to gold, the first energy identified from x-rays fluorescently emitted from the item of interest, receiving an intensity of a second energy that corresponds to gold, the second energy identified from x-rays fluorescently emitted from the item of interest. With such data available, the XRF analyzer can then calculate a ratio of measured intensities between the intensity of the first energy and the intensity of the second energy. In response to identifying that the calculated ratio is beyond a predetermined value, the XRF analyzer can then indicate that the item of interest is gold-plated.

In other embodiments, a ratio of copper or zinc lines can also be considered as an additional factor in making a determination of plating. Similar to gold, a ratio of copper lines is also monotonic and a sharp function of plate thickness. Accordingly, in some embodiments, the ratio of copper lines can be used (instead of or together with the ratio of gold lines) to determine whether an item of interest has gold plating. Relying on gold lines instead of copper lines, however, can be more beneficial because the relative error of measurement of the ratio of gold lines gets smaller with plate thickness, while the relative error of measurement of the ratio of copper lines increases with thickness. In other words, using copper line ratios is not as accurate as using gold line ratios because the error rate of using copper line ratios can be deemed unacceptable. Other embodiments can include calculating a karat value and ratio of $L\alpha/L\beta$ in a given sample (test object) and divide it by a reference ratio. If the karat value is none of known (acceptable) karatages, then the sample may be fake (gold plated). If a reference gold line ratio is more than 1.03, then the object is identified as gold plated. If a reference gold line ratio is more than 1.03 and a copper line ratio is less than 3 but more than 1, then the object can be identified as plated with 24K gold. If a reference gold line ratio is more than 1.03 and a copper line ratio is more than 4.0, then the object can be identified as plated with less than 24 K gold. If none of the above are true, then an inconclusive indication can be given, or otherwise direct the further testing is recommended.

In other embodiments, similar techniques can be implemented to identify plating from other metals or materials such as to identify silver plating versus solid silver alloy, chrome plating, rhodium plating, platinum plating, etc. Accordingly, identifying plating of other metals includes using x-ray fluorescence and measuring intensities of two or more energies of a given material or atomic element from a target item. A ratio of measured intensities between the two or more energies can then be compared to a predetermined value to determine plating. The predetermined value represents a lines intensity ratio of a given specific material/element when that specific material is essentially infinitely thick. In other words, the lines intensity ratio corresponds to a value that does not continue to change with increased thickness of the given material. Because different atomic elements have different signature characteristics, lines intensity ratio values and curves can vary among elements. Thus, embodiments to detect plating other than gold plating follow the same techniques as described for detecting gold plating, but with values and ratios modified to correspond to a specific material.

Continuing with FIG. 4, the following discussion provides a basic embodiment indicating how to carry out functionality associated with the XRF analyzer 140 as discussed above. It should be noted, however, that the actual configuration for carrying out the XRF analyzer 140 can vary depending on a respective application. For example, computer system 149 can include one or multiple computers that carry out the processing as described herein.

In different embodiments, computer system 149 may be any of various types of devices, including, but not limited to, XRF analyzer, a cell phone, a personal computer system, desktop computer, laptop, notebook, or netbook computer, mainframe computer system, handheld computer, workstation, network computer, router, network switch, bridge, application server, storage device, a consumer electronics device such as a camera, camcorder, set top box, mobile device, video game console, handheld video game device, or in general any type of computing or electronic device.

Computer system 149 is shown connected to display monitor 130 for displaying a graphical user interface 133 for a user 136 to operate using input devices 135. Repository 138 can optionally be used for storing data files and content both before and after processing. Input devices 135 can include one or more devices such as a keyboard, computer mouse, microphone, etc.

As shown, computer system 149 of the present example includes an interconnect 143 that couples a memory system 141, a processor 142, I/O interface 144, and a communications interface 145.

I/O interface 144 provides connectivity to peripheral devices such as input devices 135 including a computer mouse, a keyboard, a selection tool to move a cursor, display screen, etc.

Communications interface 145 enables the XRF analyzer 140 of computer system 149 to communicate over a network and, if necessary, retrieve any data required to create views, process content, communicate with a user, etc. according to embodiments herein.

As shown, memory system 141 is encoded with XRF analyzer 140-1 that supports functionality as discussed above and as discussed further below. XRF analyzer 140-1 (and/or other resources as described herein) can be embodied as software code such as data and/or logic instructions that support processing functionality according to different embodiments described herein.

During operation of one embodiment, processor 142 accesses memory system 141 via the use of interconnect 143 in order to launch, run, execute, interpret or otherwise perform the logic instructions of the XRF analyzer 140-1. Execution of the XRF analyzer 140-1 produces processing functionality in XRF analyzer process 140-2. In other words, the XRF analyzer process 140-2 represents one or more portions of the XRF analyzer 140 performing within or upon the processor 142 in the computer system 149.

It should be noted that, in addition to the XRF analyzer process 140-2 that carries out method operations as discussed herein, other embodiments herein include the XRF analyzer 140-1 itself (i.e., the un-executed or non-performing logic instructions and/or data). The XRF analyzer 140-1 may be stored on a non-transitory, tangible computer-readable storage medium including computer readable storage media such as floppy disk, hard disk, optical medium, etc. According to other embodiments, the XRF analyzer 140-1 can also be stored in a memory type system such as in firmware, read only memory (ROM), or, as in this example, as executable code within the memory system 141.

In addition to these embodiments, it should also be noted that other embodiments herein include the execution of the XRF analyzer 140-1 in processor 142 as the XRF analyzer process 140-2. Thus, those skilled in the art will understand that the computer system 149 can include other processes and/or software and hardware components, such as an operating system that controls allocation and use of hardware resources, or multiple processors.

Those skilled in the art will also understand that there can be many variations made to the operations of the techniques explained above while still achieving the same objectives of the invention. Such variations are intended to be covered by the scope of this invention. As such, the foregoing description of embodiments of the invention are not intended to be limiting. Rather, any limitations to embodiments of the invention are presented in the following claims.

The invention claimed is:

1. A method comprising:
   directing an x-ray excitation beam onto at least a portion of an item of interest, the x-ray excitation beam causing the item of interest to fluorescently emit x-rays at various energies;
   measuring an intensity of a first energy that corresponds to an alpha energy emission line of gold, the first energy identified from x-rays fluorescently emitted from the item of interest;
   measuring an intensity of a second energy that corresponds to a beta energy emission line of gold, the second energy identified from x-rays fluorescently emitted from the item of interest;
   calculating a ratio of measured intensities between the intensity of the first energy and the intensity of the second energy; and
   in response to identifying that the calculated ratio is beyond a predetermined value, producing an indication that the item of interest is gold-plated.

2. The method of claim 1, wherein the predetermined value is a gold lines intensity ratio representing a gold thickness of more than about 15 microns, wherein the calculated ratio is beyond the predetermined value indicating a thickness of gold less than about 15 microns.

3. The method of claim 1, wherein the predetermined value is a ratio value of approximately 0.84, and the calculated ratio is greater than 0.84.

4. The method of claim 3, wherein the predetermined value is a first predetermined value, the method further comprising:
   in response to identifying that the calculated ratio is less than a second predetermined value, indicating that the item of interest is gold-plated.

5. The method of claim 4, wherein the second predetermined value is a ratio value of approximately 0.60.

6. The method of claim 5, further comprising:
   analyzing a spectrum of x-rays fluorescently emitted from the item of interest to identify a percentage composition of silver from the item of interest relative to other elements in the item of interest;
   in response to identifying that the concentration of silver is less than about 20 percent, indicating that the item of interest is gold-plated brass; and
   in response to identifying that the concentration of silver is greater than about 20 percent, indicating that the item of interest is either gold-plated brass or gold-plated silver.

7. The method of claim 1, further comprising:
   analyzing a spectrum of x-rays fluorescently emitted from the item of interest to identify a percentage composition of gold in the item of interest with respect to other elements in the item of interest; and
   in response to identifying that the concentration of gold in the item of interest is less than about 33 percent, confirming that the item of interest is gold-plated.

8. The method of claim 7, further comprising:
   identifying a percentage composition of nickel from the item of interest relative to other elements in the item of interest by analyzing the spectrum of x-rays fluorescently emitted from the item of interest; and
   in response to identifying that the concentration of nickel is greater than about 10 percent, confirming that the item of interest is gold-plated.

9. The method of claim 7, further comprising:
   wherein identifying a percentage composition of gold includes executing bulk analysis of elemental composition of the item of interest using either an energy dispersive XRF (X-Ray Fluorescence) analyzer or a wavelength dispersive XRF analyzer.

10. The method of claim 1, wherein the item of interest is jewelry.

11. The method of claim 1, further comprising:
    in addition to indicating that the item of interest is gold-plated, indicating an approximate thickness of gold plating on the item of interest.

12. The method of claim 1, wherein the first energy corresponds to an alpha energy emission of gold around 9.71 keV; and
    wherein the second energy corresponds to a beta energy emission of gold around 11.45 keV; and
    wherein the predetermined value is a gold lines intensity ratio representing a saturation plateau of gold at which the gold lines intensity ratio is substantially constant regardless of thickness.

13. The method of claim 1, wherein calculating the ratio includes:
    dividing the measured intensity of the first energy by the measured intensity of the second energy.

14. The method of claim 13, wherein the predetermined value is a gold lines intensity ratio representing a gold thickness of more than about 15 microns, wherein the calculated ratio is greater than the predetermined value indicating a thickness of gold less than about 15 microns.

15. The method of claim 14, wherein the predetermined value is a ratio value of approximately 0.84, and the calculated ratio is greater than 0.84.

16. The method of claim 15, wherein the first energy corresponds to an alpha energy emission of gold around 9.71 keV; and
    wherein the second energy corresponds to a beta energy emission of gold around 11.45 keV.

17. The method of claim 1, wherein the predetermined value represents a gold lines intensity ratio value disposed between a first range of gold lines intensity ratios in which the sample gold lines intensity ratio for gold substantially varies depending on gold thickness and a second range of intensity ratios in which the gold lines intensity ratio is substantially constant regardless of sample gold thickness.

18. An x-ray fluorescence (XRF) analyzer comprising:
    an x-ray source that generates an x-ray excitation beam to be directed onto at least a portion of an item of interest;
    an x-ray detector positioned to receive x-rays emitted from the item of interest, the emitted x-rays including fluorescently emitted x-rays at a first energy that corresponds to an alpha energy emission line of gold, the emitted x-rays also including fluorescently emitted x-rays at a second energy that corresponds to a beta energy emission line of gold, the x-ray detector producing signals indicating intensities of the fluorescently emitted x-rays;
    a signal processor coupled to the x-ray detector, the signal processor calculating a ratio of measured intensities between an intensity of the first energy and an intensity of the second energy; and
    a display indicating that the item of interest is gold-plated in response to the signal processor identifying that the calculated ratio is beyond a predetermined value.

19. The XRF analyzer of claim 18, wherein the predetermined value is a gold lines intensity ratio representing a gold thickness of more than about 15 microns; and
    wherein the calculated ratio is greater than the predetermined value, which indicates a thickness of gold less than about 15 microns.

20. The XRF analyzer of claim 18, wherein the predetermined value is a threshold ratio value of approximately 0.84, and the calculated ratio is greater than approximately 0.84.

21. The XRF analyzer of claim 20, wherein the display further indicates that the item of interest is gold-plated in response to the signal processor identifying that the calculated ratio is less than a second predetermined value, the second predetermined value being a ratio value of approximately 0.60.

22. The XRF analyzer of claim 20, wherein the XRF analyzer is selected from the group consisting of energy dispersive XRF analyzer and wavelength dispersive XRF analyzer.

23. The XRF analyzer of claim 18, wherein the signal processor is further configured to:
    identify a percentage composition of gold from the item of interest relative to other elements in the item of interest by analyzing a spectrum of x-rays fluorescently emitted from the item of interest;
    in response to identifying that the concentration of gold is less than about 33 percent, indicate that the item of interest is gold-plated;
    identify a percentage composition of nickel from the item of interest relative to other elements in the item of interest by analyzing the spectrum of x-rays fluorescently emitted from the item of interest; and
    in response to identifying that the concentration of nickel is greater than about 10 percent, indicate that the item of interest is gold-plated.

24. The XRF analyzer of claim 18, wherein the signal processor is further configured to:
    identify a percentage composition of silver from the item of interest relative to other elements in the item of interest by analyzing a spectrum of x-rays fluorescently emitted from the item of interest;
    in response to identifying that the concentration of silver is less than about 20 percent, indicate that the item of interest is gold-plated brass; and
    in response to identifying that the concentration of silver is greater than about 20 percent, indicate that the item of interest is either gold-plated brass or gold-plated silver.

25. A computer-implemented method for identifying gold plating on objects from x-ray fluorescence (XRF), the computer-implemented method comprising:
    receiving data corresponding to x-rays that have been fluorescently emitted at various energies from an item of interest;
    receiving an intensity of a first energy that corresponds to an alpha energy emission line of gold, the first energy identified from x-rays fluorescently emitted from the item of interest;
    receiving an intensity of a second energy that corresponds to a beta energy emission line of gold, the second energy identified from x-rays fluorescently emitted from the item of interest;
    calculating a ratio of measured intensities between the intensity of the first energy and the intensity of the second energy; and
    in response to identifying that the calculated ratio is beyond a predetermined value, indicating that the item of interest is gold-plated.

26. The computer-implemented method of claim 25, wherein the predetermined value is a gold lines intensity ratio representing a gold thickness of more than about 15 microns, wherein the calculated ratio being beyond the predetermined value indicates a thickness of gold less than about 15 microns.

27. A method comprising:
    directing an x-ray excitation beam onto at least a portion of an item of interest, the x-ray excitation beam causing the item of interest to fluorescently emit x-rays at various energies;
    measuring an intensity of a first energy that corresponds to an alpha energy emission line of gold, the first energy identified from x-rays fluorescently emitted from the item of interest;
    measuring an intensity of a second energy that corresponds to a beta energy emission line of gold, the second energy identified from x-rays fluorescently emitted from the item of interest;
    calculating a ratio of measured intensities between the intensity of the first energy and the intensity of the second energy; and
    in response to identifying that the calculated ratio falls outside of a ratio range, producing an indication that the item of interest is gold-plated.

28. The method as in claim 27, wherein calculating the ratio includes dividing the intensity of the first energy in the alpha energy emission line of gold by the intensity of the second energy in the beta energy emission line of gold.

29. An apparatus comprising:
    an x-ray source, the x-ray source exposing an item of interest to x-ray excitation radiation;
    an x-ray detector positioned to receive x-rays fluorescently emitted from the item of interest; and
    a signal processor coupled to the x-ray detector, the signal processor classifying the item of interest based at least in part on a calculated ratio compared to a predetermined value, the calculated ratio derived from an intensity of fluorescently emitted energy at a first energy level from the item of interest with respect to an intensity of fluorescently emitted energy at a second energy level from the item of interest; wherein the predetermined value is a gold lines intensity ratio representing a saturation plateau of gold at which the gold lines intensity ratio is substantially constant over a range of gold thickness.

30. The apparatus as in claim 29, wherein the gold lines intensity ratio represents a gold thickness of around 15 microns, the calculated ratio greater than the predetermined value, indicating a thickness of gold on the item of interest as being less than around 15 microns.

31. The apparatus as in claim 30, wherein the calculated ratio equals the intensity of fluorescently emitted energy at the first energy level divided by the intensity of fluorescently emitted energy at the second energy level; and
    wherein the first energy level corresponds to an alpha energy emission of gold around 9.71 keV; and
    wherein the second energy level corresponds to a beta energy emission of gold around 11.45 keV.

* * * * *